United States Patent
Meyer et al.

(10) Patent No.: US 9,849,257 B2
(45) Date of Patent: Dec. 26, 2017

(54) OSCILLATING POSITIVE RESPIRATORY PRESSURE DEVICE

(71) Applicant: Trudell Medical International, London (CA)

(72) Inventors: Adam Meyer, London (CA); Dan Engelbreth, London (CA)

(73) Assignee: TRUDELL MEDICAL INTERNATIONAL, London, Ontario (CA)

( * ) Notice: Subject to any disclaimer, the term of this patent is extended or adjusted under 35 U.S.C. 154(b) by 567 days.

(21) Appl. No.: 14/462,009

(22) Filed: Aug. 18, 2014

(65) Prior Publication Data

US 2015/0053209 A1    Feb. 26, 2015

Related U.S. Application Data

(60) Provisional application No. 61/868,667, filed on Aug. 22, 2013.

(51) Int. Cl.
*A61M 16/00* (2006.01)
*A61M 16/20* (2006.01)

(52) U.S. Cl.
CPC ...... *A61M 16/0006* (2014.02); *A61M 16/208* (2013.01); *A61M 2210/0625* (2013.01)

(58) Field of Classification Search
CPC ...... A61M 11/00; A61M 11/02; A61M 11/06; A61M 15/00; A61M 15/009; A61M 16/00;

(Continued)

(56) References Cited

U.S. PATENT DOCUMENTS

| 393,869 A | 12/1888 | Warren |
| 938,808 A | 11/1909 | Yount |

(Continued)

FOREIGN PATENT DOCUMENTS

| EP | 0 372 148 A1 | 6/1990 |
| EP | 0 678 306 A2 | 10/1995 |

(Continued)

OTHER PUBLICATIONS

International Preliminary Report on Patentability for PCT/162014/064002, dated Feb. 23, 2016.

(Continued)

*Primary Examiner* — Annette Dixon
(74) *Attorney, Agent, or Firm* — Brinks Gilson & Lione

(57) ABSTRACT

A respiratory treatment device includes a housing enclosing a chamber, a chamber inlet configured to receive a flow of air into the chamber, a first chamber outlet configured to permit the flow of air to exit the chamber, and a second chamber outlet configured to permit the flow of air to exit the chamber. A vane mounted within the chamber is configured to rotate between a first position where the flow of air is directed to exit the chamber through the first chamber outlet, and a second position where the flow of air is directed to exit the chamber through the second chamber outlet. A blocking member disposed on the vane is moveable relative to the chamber inlet between a closed position where the flow of air through the chamber inlet is restricted, and an open position where the flow of air through the chamber inlet is less restricted.

19 Claims, 19 Drawing Sheets

(58) Field of Classification Search
CPC .......... A61M 16/0006; A61M 16/0057; A61M 16/0066; A61M 16/0096; A61M 16/04; A61M 16/06; A61M 16/08; A61M 16/0816; A61M 16/0833; A61M 16/0866; A61M 16/14; A61M 16/20; A61M 16/205; A61M 16/208; A61M 16/209; A61M 2205/3365; A63B 2071/0633; A63B 2071/0694; A63B 21/00069; A63B 21/00076; A63B 21/00196; A63B 2208/14; A63B 2209/08; A63B 2225/20; A63B 2230/40; A63B 23/18; B05B 7/0012; F04C 2270/0421; Y10S 128/912; Y10T 137/2544
USPC ............ 128/200.24, 201.26, 201.28, 202.27, 128/203.12, 204.18, 204.21, 204.25, 128/205.23, 205.24, 207.12, 912
See application file for complete search history.

(56) References Cited

U.S. PATENT DOCUMENTS

| | | |
|---|---|---|
| 2,670,739 A | 3/1954 | NcNeill |
| 2,918,917 A | 12/1959 | Emerson |
| 3,710,780 A | 1/1973 | Milch |
| 3,732,864 A * | 5/1973 | Thompson ........ A61M 15/0095 128/200.23 |
| 3,814,297 A * | 6/1974 | Warren ............ A61M 15/0091 128/200.23 |
| 3,908,987 A | 9/1975 | Boehringer |
| 4,054,134 A | 10/1977 | Kritzer |
| 4,062,358 A | 12/1977 | Kritzer |
| 4,182,366 A | 1/1980 | Boehringer |
| 4,198,969 A | 4/1980 | Virag |
| 4,221,381 A | 9/1980 | Ericson |
| 4,226,233 A | 10/1980 | Kritzer |
| 4,231,375 A | 11/1980 | Boehringer et al. |
| 4,267,832 A | 5/1981 | Hakkinen |
| 4,275,722 A | 6/1981 | Sorensen |
| 4,298,023 A | 11/1981 | McGinnis |
| 4,327,740 A | 5/1982 | Shuman |
| 4,403,616 A | 9/1983 | King |
| 4,436,090 A | 3/1984 | Darling |
| 4,470,412 A | 9/1984 | Nowacki et al. |
| 4,601,465 A | 7/1986 | Roy |
| 4,611,591 A | 9/1986 | Inui et al. |
| 4,635,631 A | 1/1987 | Izumi |
| 4,651,731 A | 3/1987 | Vicenzi et al. |
| 4,664,107 A * | 5/1987 | Wass ................ A61M 15/0091 128/200.23 |
| 4,739,987 A | 4/1988 | Nicholson |
| 4,770,413 A | 9/1988 | Green |
| 4,973,047 A | 11/1990 | Norell |
| 4,981,295 A | 1/1991 | Belman et al. |
| 5,018,517 A | 5/1991 | Liardet |
| 5,042,467 A | 8/1991 | Foley |
| 5,065,746 A | 11/1991 | Steen |
| 5,193,529 A | 3/1993 | Labaere |
| 5,345,930 A | 9/1994 | Cardinal et al. |
| 5,381,789 A | 1/1995 | Marquardt |
| 5,451,190 A | 9/1995 | Liardet |
| 5,479,920 A | 1/1996 | Piper et al. |
| 5,540,220 A | 7/1996 | Gropper et al. |
| 5,569,122 A | 10/1996 | Cegla |
| 5,570,682 A | 11/1996 | Johnson |
| 5,598,839 A | 2/1997 | Niles et al. |
| 5,613,489 A | 3/1997 | Miller |
| 5,645,049 A | 7/1997 | Foley et al. |
| 5,647,345 A | 7/1997 | Saul |
| 5,655,520 A | 8/1997 | Howe |
| 5,658,221 A | 8/1997 | Hougen |
| 5,687,912 A * | 11/1997 | Denyer ................ A61M 11/06 128/200.21 |
| 5,791,339 A | 8/1998 | Winter |
| 5,829,429 A | 11/1998 | Hughes |
| 5,848,588 A | 12/1998 | Foley et al. |
| 5,862,802 A | 1/1999 | Bird |
| 5,890,998 A | 4/1999 | Hougen |
| 5,893,361 A | 4/1999 | Hughes |
| 5,899,832 A | 5/1999 | Hougen |
| 5,910,071 A | 6/1999 | Hougen |
| 5,925,831 A | 7/1999 | Storsved |
| 6,026,807 A | 2/2000 | Puderbaugh et al. |
| 6,044,841 A | 4/2000 | Verdun et al. |
| 6,058,932 A | 5/2000 | Hughes |
| 6,066,101 A | 5/2000 | Johnson |
| 6,067,984 A | 5/2000 | Piper |
| 6,083,141 A | 7/2000 | Hougen |
| 6,089,105 A | 7/2000 | Ricciardelli |
| 6,102,038 A | 8/2000 | DeVries |
| 6,167,881 B1 | 1/2001 | Hughes |
| 6,176,235 B1 | 1/2001 | Benarrouch et al. |
| D440,651 S | 4/2001 | Foran |
| 6,240,917 B1 | 6/2001 | Andrade |
| 6,253,766 B1 | 7/2001 | Niles |
| 6,293,279 B1 | 9/2001 | Schmidt et al. |
| 6,340,025 B1 | 1/2002 | Van Brunt |
| 6,345,617 B1 | 2/2002 | Engelbreth et al. |
| 6,412,481 B1 | 7/2002 | Bienvenu et al. |
| 6,500,095 B1 | 12/2002 | Hougen |
| 6,557,549 B2 | 5/2003 | Schmidt et al. |
| 6,581,595 B1 | 6/2003 | Murdock et al. |
| 6,581,596 B1 | 6/2003 | Truitt |
| 6,581,598 B1 * | 6/2003 | Foran .................... A61M 16/08 128/204.19 |
| 6,581,600 B2 | 6/2003 | Bird |
| 6,595,203 B1 | 7/2003 | Bird |
| 6,606,989 B1 | 8/2003 | Brand |
| 6,615,831 B1 | 9/2003 | Tuitt |
| 6,631,721 B1 | 10/2003 | Salter et al. |
| 6,659,100 B2 | 12/2003 | O'Rourke |
| 6,702,769 B1 | 3/2004 | Fowler-Hawkins |
| 6,708,690 B1 * | 3/2004 | Hete ................. A61M 16/0096 128/204.18 |
| 6,708,691 B1 | 3/2004 | Hayek |
| 6,726,598 B1 | 4/2004 | Jarvis |
| D490,519 S | 5/2004 | Pelerossi et al. |
| 6,776,159 B2 | 8/2004 | Pelerossi et al. |
| 6,848,443 B2 | 2/2005 | Schmidt et al. |
| 6,851,425 B2 | 2/2005 | Jaffre |
| 6,904,906 B2 | 6/2005 | Salter |
| 6,923,181 B2 | 8/2005 | Tuck |
| 6,929,007 B2 | 8/2005 | Emerson |
| 6,984,214 B2 | 1/2006 | Fowler-Hawkins |
| 7,059,324 B2 | 6/2006 | Pelerossi et al. |
| 7,096,866 B2 | 8/2006 | Be'eri et al. |
| 7,134,434 B2 | 11/2006 | Truitt et al. |
| 7,165,547 B2 | 1/2007 | Truitt et al. |
| 7,188,621 B2 | 3/2007 | DeVries |
| 7,191,776 B2 | 3/2007 | Niles |
| 7,191,780 B2 | 3/2007 | Faram |
| 7,214,170 B2 | 5/2007 | Sumners et al. |
| 7,617,821 B2 | 11/2009 | Hughes |
| 7,699,054 B2 | 4/2010 | Pelerossi et al. |
| 7,717,847 B2 | 5/2010 | Smith |
| 7,771,472 B2 | 8/2010 | Hendricksen |
| 7,779,841 B2 | 8/2010 | Dunsmore et al. |
| 7,798,148 B2 | 9/2010 | Doshi |
| 7,856,979 B2 | 12/2010 | Doshi |
| 7,909,033 B2 | 3/2011 | Faram |
| 8,006,922 B2 | 8/2011 | Katzer |
| 8,025,051 B2 | 9/2011 | Dagsland |
| 8,025,054 B2 | 9/2011 | Dunsmore et al. |
| 8,043,236 B2 | 10/2011 | Goldshtein et al. |
| 8,051,854 B2 | 11/2011 | Faram |
| RE43,174 E | 2/2012 | Schmidt et al. |
| 8,118,024 B2 | 2/2012 | Devries et al. |
| 8,225,785 B2 | 7/2012 | Richards et al. |
| 8,327,849 B2 | 12/2012 | Grychowski et al. |
| 8,460,223 B2 | 6/2013 | Huster et al. |
| 8,469,029 B2 | 6/2013 | Brown et al. |
| 8,485,179 B1 | 7/2013 | Meyer |
| 8,539,951 B1 | 9/2013 | Meyer et al. |

(56) References Cited

U.S. PATENT DOCUMENTS

| | | |
|---|---|---|
| 2007/0259759 A1 | 11/2007 | Sumners et al. |
| 2008/0053456 A1 | 3/2008 | Brown et al. |
| 2008/0156319 A1* | 7/2008 | Avni .................... A61M 11/005 128/200.14 |
| 2010/0139655 A1 | 6/2010 | Genosar |
| 2010/0307487 A1 | 12/2010 | Dunsmore et al. |
| 2011/0290240 A1 | 12/2011 | Meyer et al. |
| 2012/0097164 A1 | 4/2012 | Rozario et al. |
| 2012/0304988 A1 | 12/2012 | Meyer |
| 2013/0133649 A1 | 5/2013 | Grychowski et al. |
| 2013/0284171 A1 | 10/2013 | Adam et al. |
| 2013/0312746 A1 | 11/2013 | Grychowski |
| 2014/0041657 A1 | 2/2014 | Meyer |
| 2014/0150790 A1 | 6/2014 | Meyer |
| 2015/0151060 A1 | 6/2015 | Grychowski et al. |
| 2015/0224269 A1 | 8/2015 | Alizoti et al. |
| 2015/0297848 A1 | 10/2015 | Meyer et al. |
| 2015/0374939 A1 | 12/2015 | Meyer et al. |
| 2016/0136369 A1 | 5/2016 | Meyer et al. |
| 2016/0310695 A1 | 10/2016 | Meyer et al. |
| 2017/0028161 A1 | 2/2017 | Meyer et al. |
| 2017/0049979 A1 | 2/2017 | Meyer et al. |

FOREIGN PATENT DOCUMENTS

| | | |
|---|---|---|
| EP | 1435251 | 12/2003 |
| EP | 1 464 357 A1 | 10/2004 |
| EP | 1 435 251 B1 | 6/2006 |
| EP | 1 103 287 B1 | 6/2007 |
| EP | 1 897 576 A1 | 3/2008 |
| EP | 1 908 489 A1 | 4/2008 |
| EP | 2444114 | 4/2012 |
| EP | 2455137 | 5/2012 |
| GB | 2 425 488 A | 11/2006 |
| WO | WO 89/03707 A1 | 5/1989 |
| WO | WO 96/40376 | 12/1996 |
| WO | WO 99/16490 | 4/1999 |
| WO | WO 00/27455 | 5/2000 |
| WO | WO 2007/061648 A3 | 5/2007 |
| WO | WO 2007/119104 A3 | 10/2007 |
| WO | WO 2008/063966 A1 | 5/2008 |
| WO | WO 2008/122045 A1 | 10/2008 |
| WO | WO 2009/131965 | 10/2009 |
| WO | WO 2011/058470 | 5/2011 |
| WO | WO 2012/038864 A2 | 3/2012 |
| WO | WO2012168780 A2 | 12/2012 |
| WO | WO 2014/202923 | 12/2014 |
| WO | WO 2014/202924 | 12/2014 |
| WO | WO 2014/203115 | 12/2014 |

OTHER PUBLICATIONS

U.S. Appl. No. 29/438,878, filed Dec. 4, 2012, Meyer.
U.S. Appl. No. 13/966,759, filed Aug. 14, 2013, Meyer.
Web page entitled Bronchial Hygiene, acapella Vibratory PEP Therapy System accessed from http://www.smiths-medical.com/catalog/bronchial-hygiene/acapella/acapella.html on Jul. 7, 2009.
Web page entitled Thayer Quake accessed from http://www.thayermedical.com/quake.htm on Jul. 7, 2009.
Human growth hormone, cortisol, and acid-base balance changes after hyperventilation and breath-holding; PubMed—indexed for Medline; Int J Sports Med., Dec. 1986; 7(6):311-5, Djarova T.
Bosco C, Cardinale M. & Tsarpela O (1999). Influence of vibration on mechanical power and electromyogram activity in human arm flexor muscles. Eur J Appl Physiol 79, 306-311.
David Sumners; Power Breathing and Strength; http://EzineArticles.com/972576 Published: Feb. 7, 2008.
Good Vibrations blog; http://vibrotraining.blogspot.com, Earliest posting Jan. 17, 2008.
Breathtaking News; More Youbreathe; Aug. 10, 2007.
PCT International Search Report for PCT/IB2012/001089, dated Oct. 5, 2012.
PCT International Written Opinion for PCT/IB2012/001089, dated Oct. 5, 2012.
U.S. Appl. No. 14/674,494, filed Mar. 31, 2015, Meyer et al.
U.S. Appl. No. 15/415,524, filed Jan. 25, 2017, Meyer et al.
U.S. Appl. No. 15/453,767, filed Mar. 8, 2017, Meyer et al.

\* cited by examiner

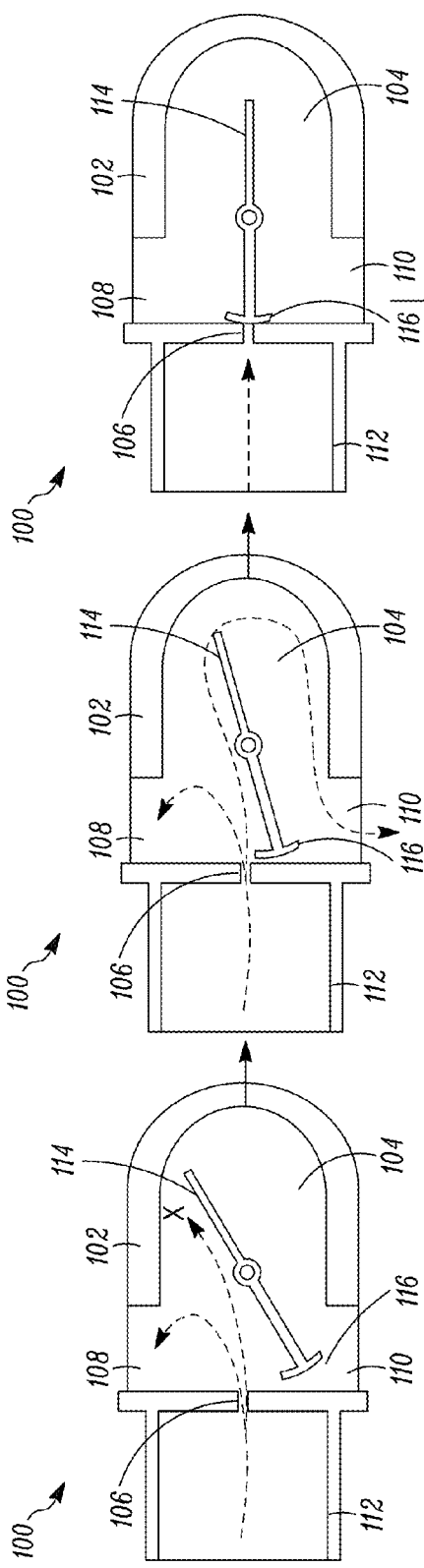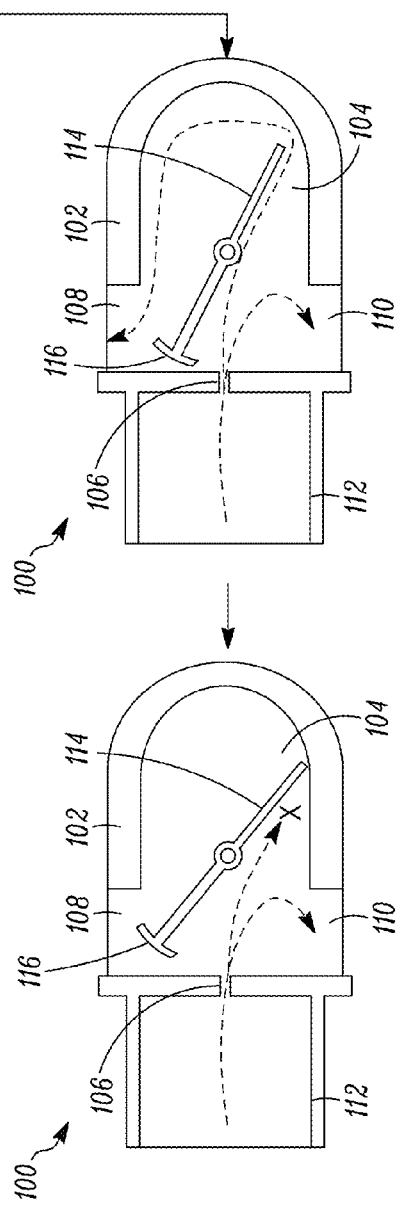

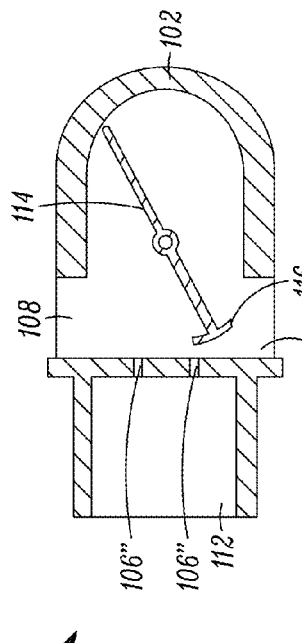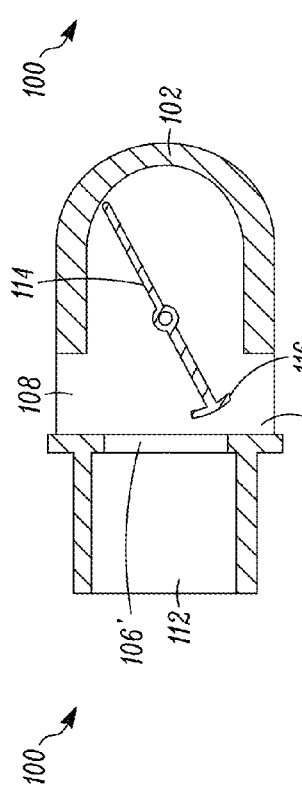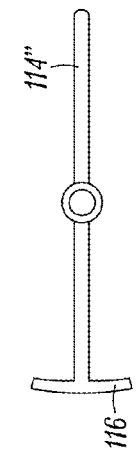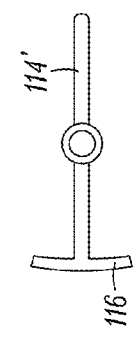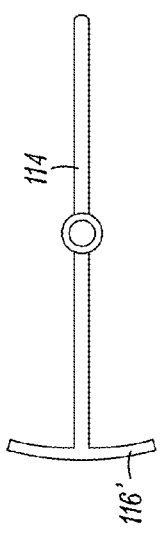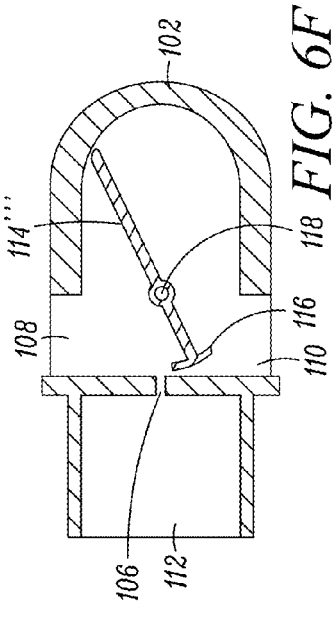

OSCILLATING POSITIVE RESPIRATORY PRESSURE DEVICE

RELATED APPLICATION

This application claims the benefit of U.S. Provisional Application No. 61/868,667, filed on Aug. 22, 2013, pending, which is incorporated herein by reference.

TECHNICAL FIELD

The present disclosure relates to a respiratory treatment device, and in particular, to an oscillating positive respiratory pressure device.

BACKGROUND

Each day, humans may produce upwards of 30 milliliters of sputum, which is a type of bronchial secretion. Normally, an effective cough is sufficient to loosen secretions and clear them from the body's airways. However, for individuals suffering from more significant bronchial obstructions, such as collapsed airways, a single cough may be insufficient to clear the obstructions.

One type of therapy, utilizing oscillating positive expiratory pressure ("OPEP"), is often used to address this issue. OPEP therapy represents an effective bronchial hygiene technique for the removal of bronchial secretions in the human body and is an important aspect in the treatment and continuing care of patients with bronchial obstructions, such as those suffering from chronic obstructive lung disease. It is believed that OPEP therapy, or the oscillation of exhalation pressure at the mouth during exhalation, effectively transmits an oscillating back pressure to the lungs, thereby splitting open obstructed airways and loosening the secretions contributing to bronchial obstructions.

OPEP therapy is an attractive form of treatment because it can be easily taught to most hospitalized patients, and such patients can assume responsibility for the administration of OPEP therapy throughout their hospitalization and also once they have returned home. To that end, a number of portable OPEP devices have been developed.

BRIEF SUMMARY

In one aspect, a respiratory treatment device includes a housing enclosing a chamber, a chamber inlet configured to receive a flow of air into the chamber, a first chamber outlet configured to permit the flow of air to exit the chamber, and a second chamber outlet configured to permit the flow of air to exit the chamber. A vane mounted within the chamber is configured to rotate between a first position where the flow of air is directed to exit the chamber through the first chamber outlet, and a second position where the flow of air is directed to exit the chamber through the second chamber outlet. A blocking member disposed on the vane is moveable relative to the chamber inlet between a closed position where the flow of air through the chamber inlet is restricted, and an open position where the flow of air through the chamber inlet is less restricted.

In another aspect, the vane may be configured to rotate in response to the flow of air into the chamber. The vane may be configured to repeatedly reciprocate between the first position and the second position in response to the flow of air into the chamber. The vane may also be prohibited from completing a complete revolution.

In another aspect, a size of the blocking member may be greater than a size of the chamber inlet. Alternatively, a size of the blocking member may be less than a size of the chamber inlet.

In another aspect, an axis of rotation of the vane may be offset from a center of the vane.

In another aspect, the respiratory treatment also includes a mouthpiece, wherein a cross sectional area of the mouthpiece is larger than a cross sectional area of the chamber inlet. In addition, an inhalation port may be in communication with the mouthpiece, the inhalation port having a one-way valve configured to open upon inhalation and close upon exhalation.

In yet another aspect, a respiratory treatment device includes a housing enclosing a chamber, an inlet configured to receive a flow of air into the chamber, and an outlet configured to permit the flow of air to exit chamber. A blocking member mounted in the chamber is moveable relative to the chamber outlet between a closed position where the flow of air through the exit is restricted, and an open position where the flow of air through the chamber outlet is less restricted. At least one vane rotatably mounted in the chamber is configured to move the blocking member between the closed position and the open position in response to the flow of air into the chamber.

In another aspect, the blocking member may be connected to the at least one vane by a shaft and at least one linkage. The shaft and the at least one linkage may cooperate to move the blocking member in linear reciprocating motion.

In another aspect, the blocking member may be configured to move between the open position and the closed position in response to contact from an arm connected to the at least one vane.

In another aspect, the blocking member may be biased toward the open position.

In another aspect, the at least one vane comprises a turbine having a plurality of vanes.

In another aspect, the chamber comprises a first portion enclosing the at least one vane and a second portion enclosing the blocking member. The first portion may be in communication with the second portion.

In another aspect, the respiratory treatment also includes a mouthpiece, wherein a cross sectional area of the mouthpiece is larger than a cross sectional area of the chamber inlet. In addition, an inhalation port may be in communication with the mouthpiece, the inhalation port having a one-way valve configured to open upon inhalation and close upon exhalation.

In yet another aspect, a method of performing respiratory treatment includes receiving a flow of air into a device having an inlet configured to receive a flow of air into the device, a first outlet configured to permit the flow air to exit the device, and a second outlet configured to permit the flow of air to exit the device. The method further includes rotating a vane mounted within the device repeatedly between a first position where the flow of air is directed to exit the chamber through the first chamber outlet, and a second position where the flow of air is directed to exit the chamber through the second chamber outlet. The method also includes moving a blocking member disposed on the vane relative to the chamber inlet between a closed position where the flow of air through the chamber inlet is restricted, and an open position where the flow of air through the chamber inlet is less restricted.

BRIEF DESCRIPTION

FIGS. 5A-5E are cross-sectional views illustrating the operation of the OPEP device of FIG. 1;

FIGS. 6A-6F are cross-section views illustrating exemplary modifications to the OPEP device of FIG. 1;

DETAILED DESCRIPTION

Figure 1:
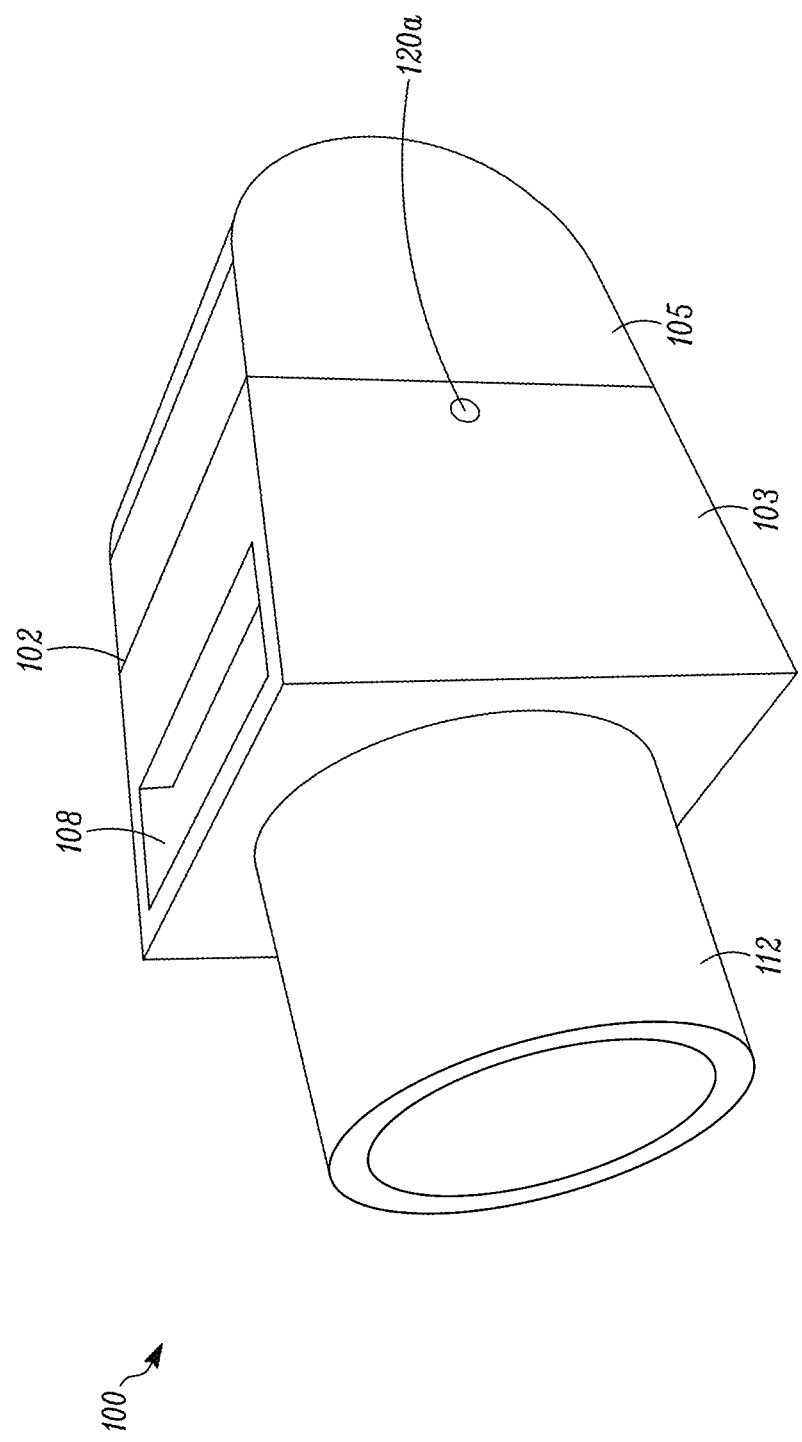
FIG. 1 is a front perspective view of a first embodiment of an OPEP device.
Figure 2:
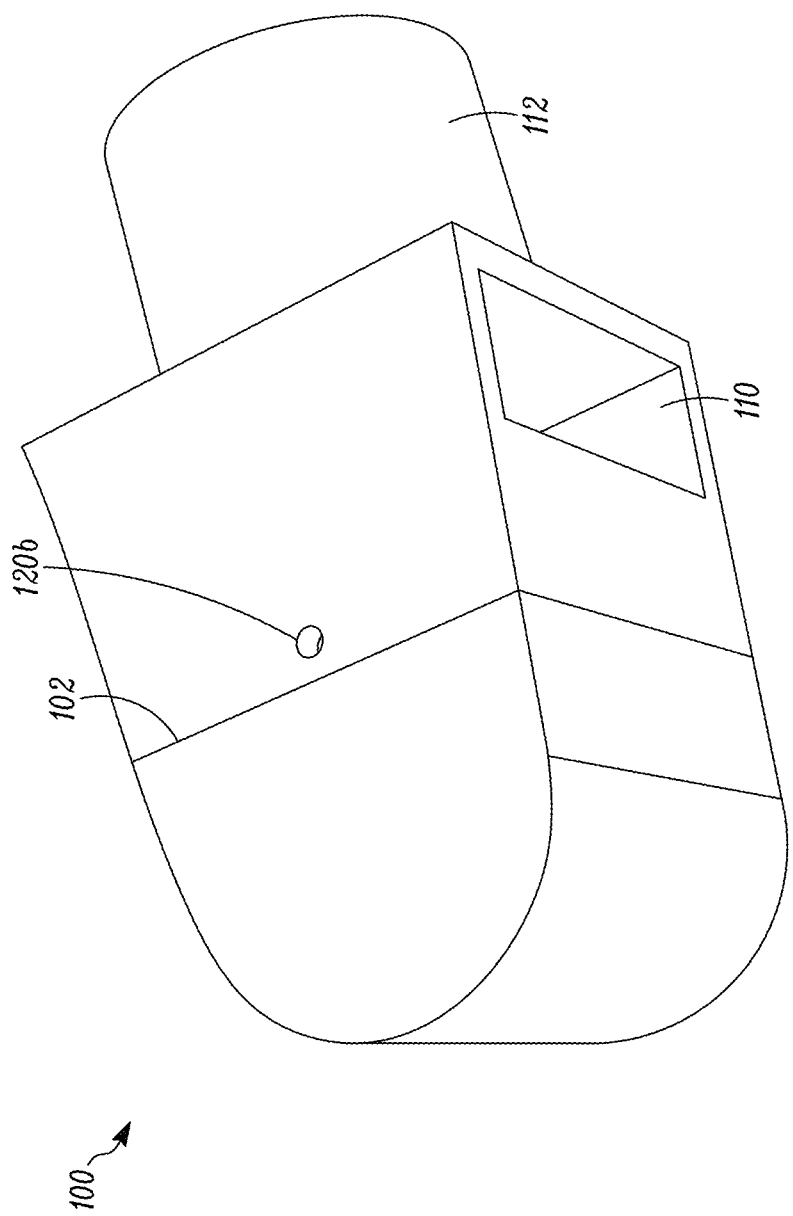
FIG. 2 is a rear perspective view of the OPEP device of FIG. 1.

Referring to FIGS. 1-4, a first embodiment of an OPEP device 100 is shown. In general, the OPEP device 100 includes a housing 102 enclosing a chamber 104, a chamber inlet 106, a first chamber outlet 108, a second chamber outlet 110, a mouthpiece 112 in communication with the chamber inlet 106, a vane 114 mounted within the chamber 104, and a blocking member 116 disposed on the vane 114.

The housing 102 and OPEP device 100 components may be constructed of any durable material, such as a low friction plastic or polymer, and may include a front section 103 and a rear section 105 that are removably attachable such that the chamber 104 may be periodically accessed for cleaning and/or replacement of the vane 114. In addition, although the mouthpiece 112 is shown as being fixedly attached to the housing 102, it is envisioned that the mouthpiece 112 may be removeable and replaceable with a mouthpiece of a different shape or size. Preferably, the size or cross-sectional area of the mouthpiece 112 is greater than the size or cross-sectional area of the chamber inlet 106. It is envisioned that other user interfaces, such as breathing tubes or gas masks (not shown), may alternatively be associated with the housing 102.

Figure 3:
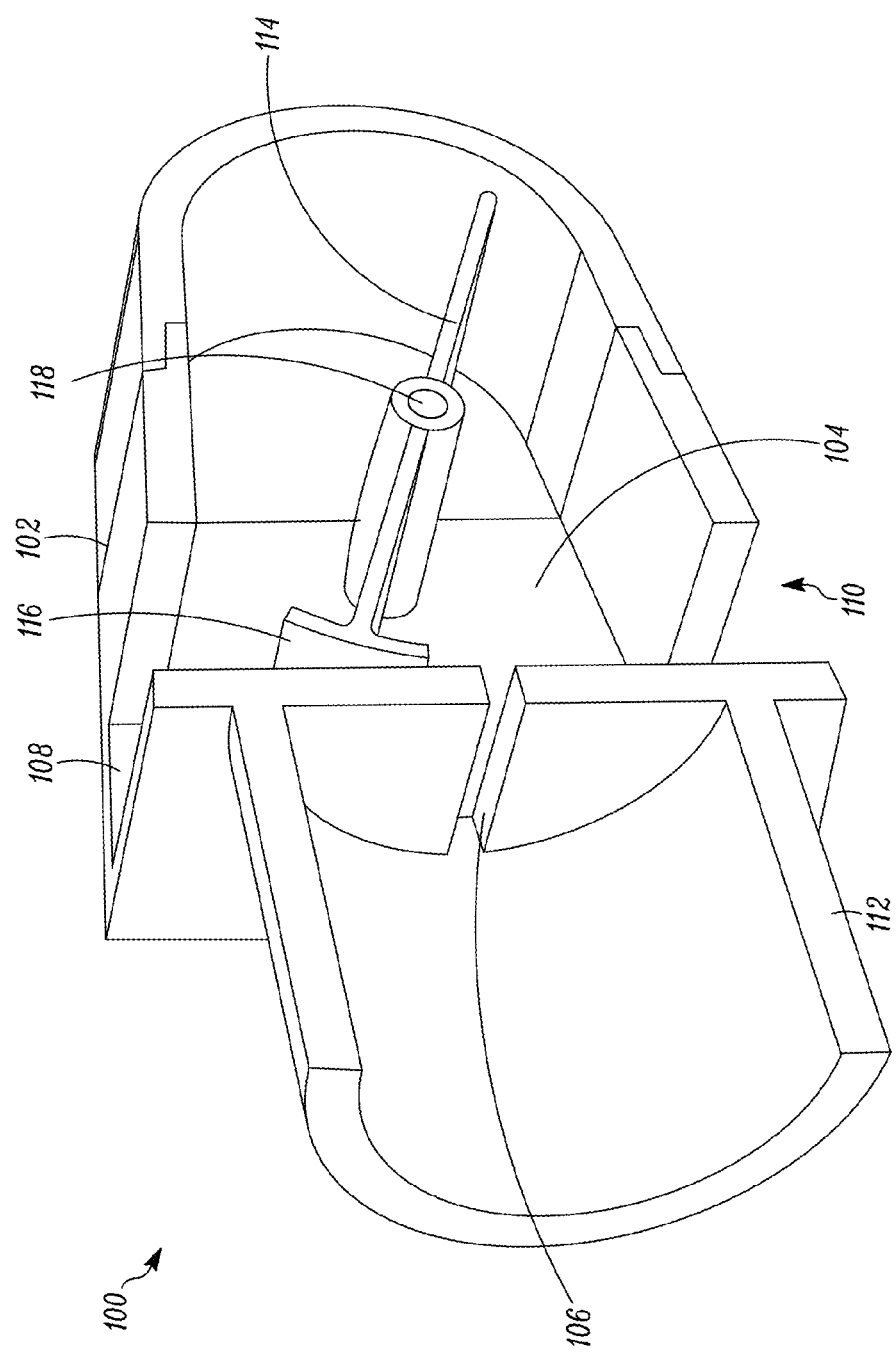
FIG. 3 is a cross-sectional perspective view of the OPEP device of FIG. 1.
Figure 4:
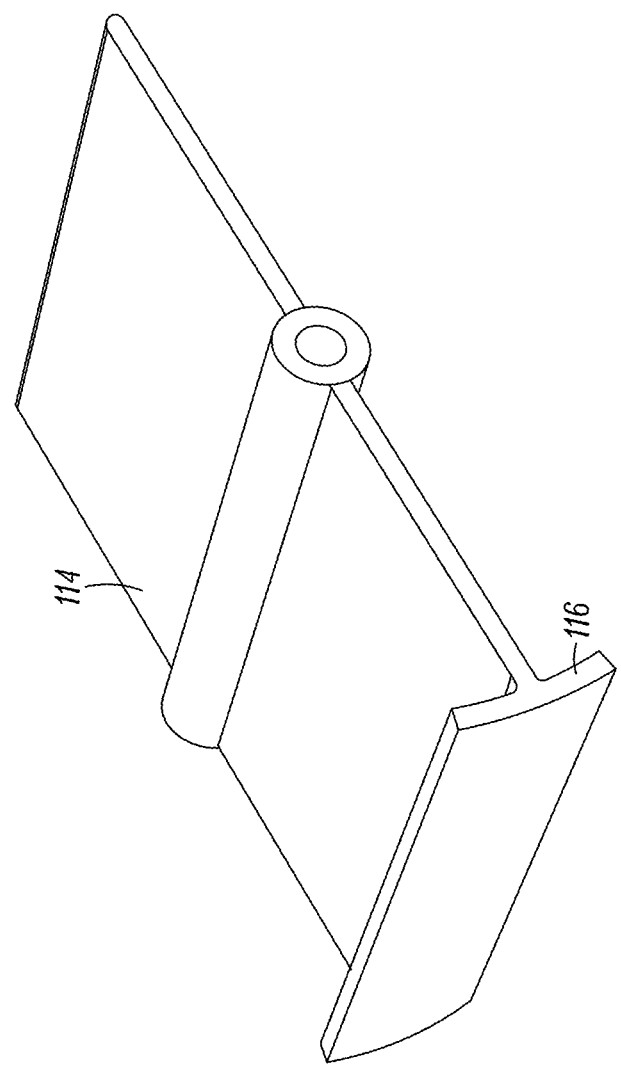
FIG. 4 is a perspective view of a blocking member disposed on a vane mountable within the OPEP device of FIG. 1.
Figure 7:
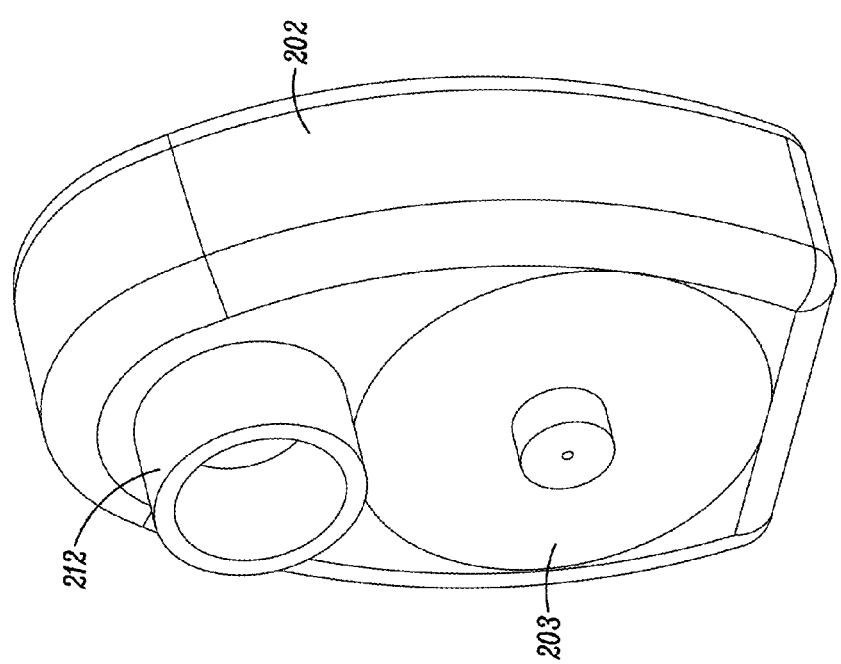
FIG. 7 is a front perspective view of a second embodiment of an OPEP device.
Figure 8:
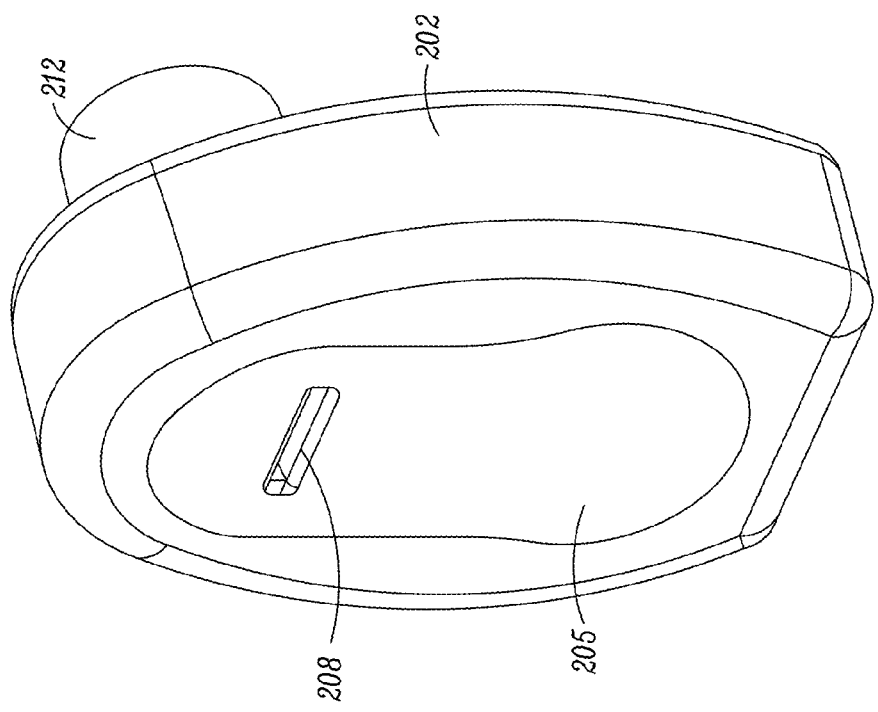
FIG. 8 is a rear perspective view of the OPEP device of FIG. 7.

As shown in FIG. 3, the vane 114 is rotatably mounted within the chamber 104 about a shaft 118. The shaft 118 may be supported by bearings 120a, 120b formed in the housing 102. As shown in FIG. 4, the vane 114 is formed as a generally planar member adapted for rotation about the shaft 118 positioned at the center of the vane 114. Alternatively, the vane 114 could be formed with any number of curves or contours. A blocking member 116 is disposed on an end of the vane 114 and is adapted to move relative to the chamber inlet 106 between an closed position, where the flow of air through the chamber inlet 106 is restricted by the blocking member 116, and an open position where the flow of air through the chamber inlet 106 is less restricted. As shown, the blocking member 116 is curved, such that it may travel in close proximity to the chamber inlet 106. The blocking member 116 is also sized and shaped such that the flow of air through the chamber inlet 106 may be completed restricted when the blocking member 116 is in a closed position. As discussed below, it is envisioned that the blocking member 116 and/or the chamber inlet 106 could be any number of shapes and sizes, and that the blocking member 116 may only partially restrict the flow of air through the chamber inlet 106 when the blocking member 116 is in a closed position.

The operation of the OPEP device 100 will now be described with reference to the illustrations shown in FIGS. 5A-5E. In FIGS. 5A-5E, the flow of air through the device 100 is illustrated by dashed lines. However, it should be appreciated that the dashed lines are exemplary and provided for purposes of illustration. The actual flow air through the device 100 may traverse any number of flow paths.

As shown in FIG. 5A, administration of OPEP therapy using the OPEP device 100 begins with the vane 114 in a first position, and the blocking member 116 in an open position. With the vane 114 in this position, exhaled air flowing into the mouthpiece 112 enters the chamber 104 through the chamber inlet 106, where it is directed by the vane 114 toward the rear portion of the of the chamber 104, denoted in FIG. 5A by "X", and generally toward the first chamber outlet 108. Although some of the exhaled air exits the OPEP device 100 through the first chamber outlet 108, as a user continues to exhale, the pressure in the rear portion of the chamber 104 increases, causing the vane 114 to begin to rotate in a clockwise direction.

As a user continues to exhale, the vane 114 rotates from the position shown in FIG. 5A to the position shown in FIG. 5B. In this position, exhaled air flowing into the chamber 104 may exit the chamber 104 through the first chamber outlet 108, or flow around the vane 114 and exit the chamber 104 through the second chamber outlet 110. The blocking member 116 in this position is also partially restricting the flow of air through the chamber inlet 106, thereby causing the pressure in the mouthpiece 112 to increase. In this position, some of the exhaled air exits the OPEP device 100 through the first chamber outlet 108. However, as a user continues to exhale, pressure in the rear of the chamber 104, along with the flow of air around the vane 114, cause the vane 114 to continue to rotate in a clockwise direction.

As a user continues to exhale, the vane 114 rotates from the position shown in FIG. 5B to the position shown in FIG. 5C. In this position, the blocking member 116 is in a closed position, and exhaled air is completely restricted from flowing through the chamber inlet 106 into the chamber 104, thereby causing the pressure in the mouthpiece 112 to rapidly increase. In this position, the momentum of the vane 114 and the blocking member 116 continue to drive the vane 114 in a clockwise direction.

As the vane 114 continues to rotate in a clockwise direction, the vane 114 rotates from the position shown in FIG. 5C to the position shown in FIG. 5D. In this position, exhaled air flowing into the chamber 104 may exit the chamber 104 through the second chamber outlet 110, or flow around the vane 114 and exit the chamber 104 through the first chamber outlet 108. In this position, the momentum of the vane 114 and the blocking member 116 is sufficient to overcome any opposing forces and continue rotating the vane 114 in a clockwise direction.

As the vane 114 continues to rotate in a clockwise direction, the vane 114 rotates from the position shown in FIG. 5D to the position shown in FIG. 5E. Additional rotation of the vane 114 is prevented if the vane 114 contacts the housing 102. With the vane 114 in this position, exhaled air flowing into the mouthpiece 112 enters the chamber 104 through the chamber inlet 106, where it is directed by the vane 114 toward the rear portion of the of the chamber 104, denoted in FIG. 5E by "X", and generally toward the second chamber outlet 110. Although some of the exhaled air exits the OPEP device 100 through the second chamber outlet 110, as a user continues to exhale, the pressure in the rear portion of the chamber 104 increases, causing the vane 114 to begin to rotate in a counter clockwise direction, repeating the cycle described above, although in reverse order.

During a period of exhalation, the vane 114 rotates repeatedly between the first position and the second position in clockwise and counter-counterclockwise directions. As this movement is repeated, the blocking member 116 moves repeatedly between a closed position, where the flow of air through the chamber inlet 106 is restricted by the blocking member 116, and an open position, where the flow of air through the chamber inlet 106 is less restricted. Consequently, the pressure in the mouthpiece 112, or user interface, oscillates between a higher pressure and a lower pressure, which pressures are in turn transmitted to the user's airways, thereby administering OPEP therapy.

Turning to FIGS. 6A-6F, various modifications to the OPEP device 100 are shown. As shown in FIGS. 6A and 6B, exemplary modifications to the chamber inlet 106 are shown. Whereas the chamber inlet 106 shown in FIG. 3 is sized and shaped as a long and narrow horizontal opening, as shown in FIG. 6A, a chamber inlet 106' may be sized and shaped as a long and narrow opening, or as shown in FIG. 6B, a chamber inlet 106" may be sized and shaped as two narrow openings. It is also envisioned that the opening could be shaped as a cross, a circle, a square, or any other number of shapes, or combination of shapes. In this way, the shape and size of the chamber inlet 106 may be selected to achieve the desired performance of the OPEP device 100.

As shown in FIGS. 6C-6F, exemplary modification to the vane 114 and the blocking member 116 are shown. For example, as compared to the blocking member 116 shown in FIGS. 3-4, a blocking member 116' shown in FIG. 6C is larger, thereby restricting the flow of air through the chamber inlet 106 for a longer period while the blocking member 116' is in a closed position. Similarly, as compared to the vane 114 shown in FIGS. 3-4, a vane 114' and a vane 114" are shorter in length, thereby changing the speed or frequency at which the vanes rotate, and the pressures at which the OPEP device 100 operates. In general, a shorter vane will oscillate faster, while a longer vane will oscillate slower. Finally, as shown in FIG. 6F, a vane 114''' is configured to have an axis of rotation, or the position of the shaft 118, offset from a center of the vane 114'''. It is also envisioned that the total rotation of a vane may be selected or adjusted, for example, by changing the length of the vane while maintaining the size of the housing, or by providing a stop in the housing that limits the rotation of the vane. In general, an increase in the amount of rotation will result in a decreased frequency, while a decrease in the amount of rotation will result in an increased frequency.

Referring to FIGS. 7-13, a second embodiment of an OPEP device 200 is shown. In general, the OPEP device 200 includes a housing 202 enclosing a chamber 204 having a first portion 207 and a second portion 209 joined by a passage 211, a chamber inlet 206, a chamber outlet 208, a mouthpiece 212 in communication with the chamber inlet 206, a turbine 214 rotatably mounted within the chamber 204 via a shaft 218, a blocking member 216, a first linkage 220, and a second linkage 222.

The housing 202 and OPEP device 200 components may be constructed of any durable material, such as a low friction plastic or polymer, and may include a front cover 203 and a rear cover 205 that are removably attachable such that the chamber 204 may be periodically accessed for cleaning and/or replacement of the turbine 214 and/or linkages 220, 222. In addition, although the mouthpiece 212 is shown as being fixedly attached to the housing 202, it is envisioned that the mouthpiece 212 may be removeable and replaceable with a mouthpiece of a different shape or size. Preferably, the size or cross-sectional area of the mouthpiece 212 is greater than the size or cross-sectional area of the chamber inlet 206. It is envisioned that other user interfaces, such as breathing tubes or gas masks (not shown), may alternatively be associated with the housing 202.

Figure 9:
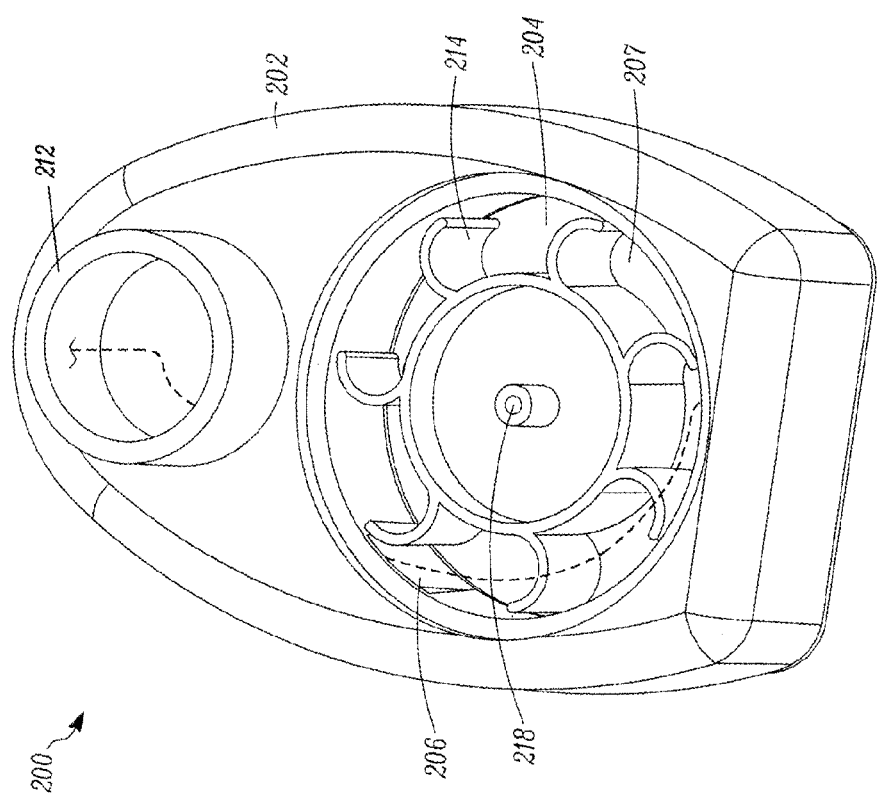
FIG. 9 is a perspective view of the OPEP device of FIG. 7, shown with a font cover of the device removed.
Figure 10:
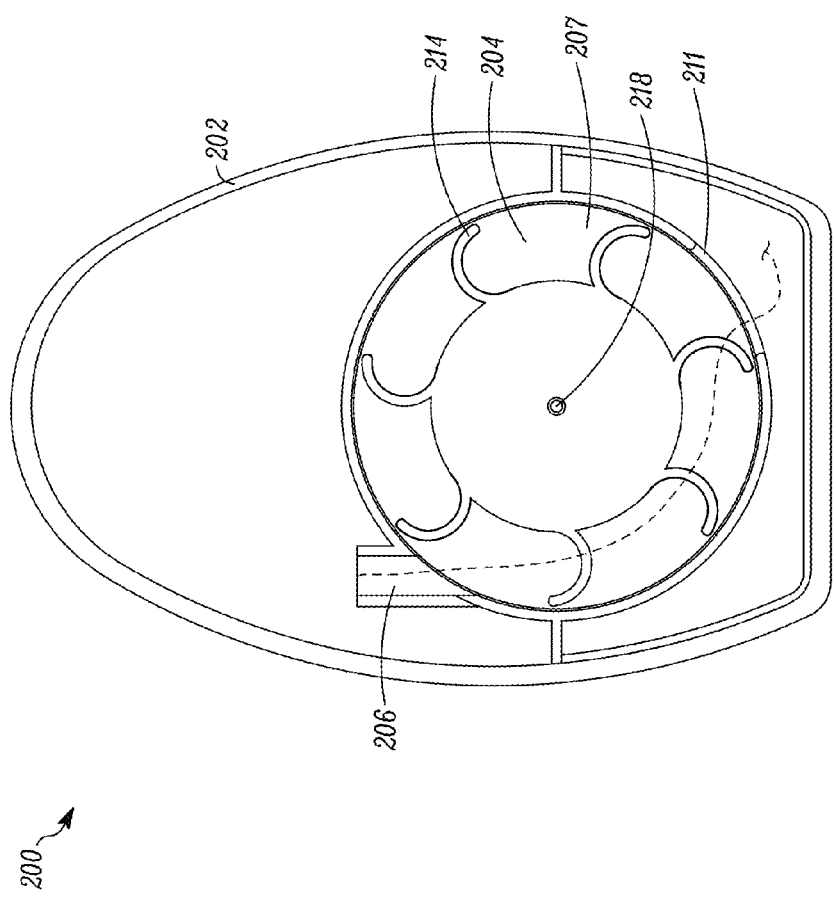
FIG. 10 is a cross-sectional view of the OPEP device of FIG. 7.
Figure 11:
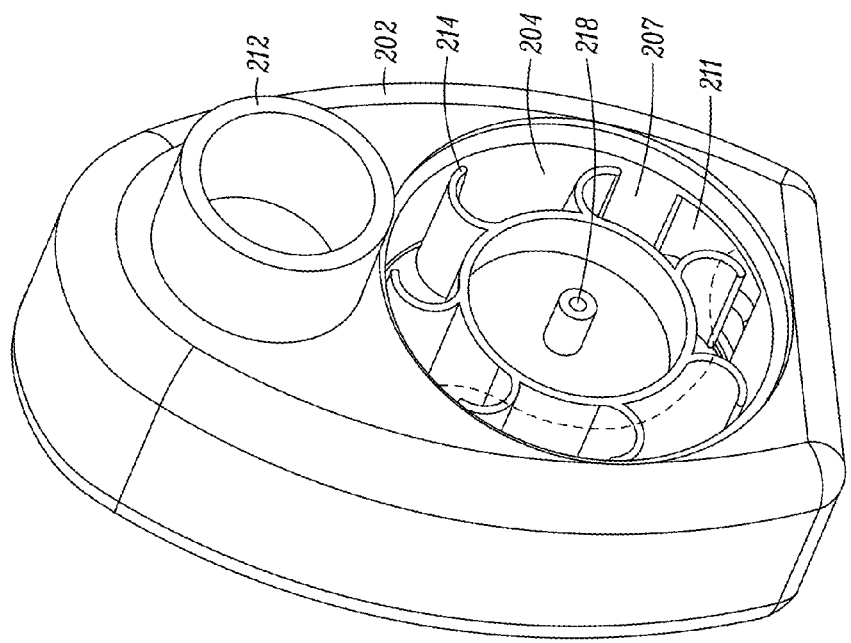
FIG. 11 is a perspective view of the OPEP device of FIG. 7, shown with the front cover of the device removed.

As shown in FIGS. 9-11, the turbine 214 is rotatably mounted via the shaft 218 within the first portion 207 of the chamber 204 and is configured to rotate in response to a flow of air through the chamber inlet 206. As shown, the turbine 214 includes a plurality of vanes, although it is envisioned that the turbine could have as few as one vane, or many more vanes. The size and shape of the vanes may also vary.

Figure 12:
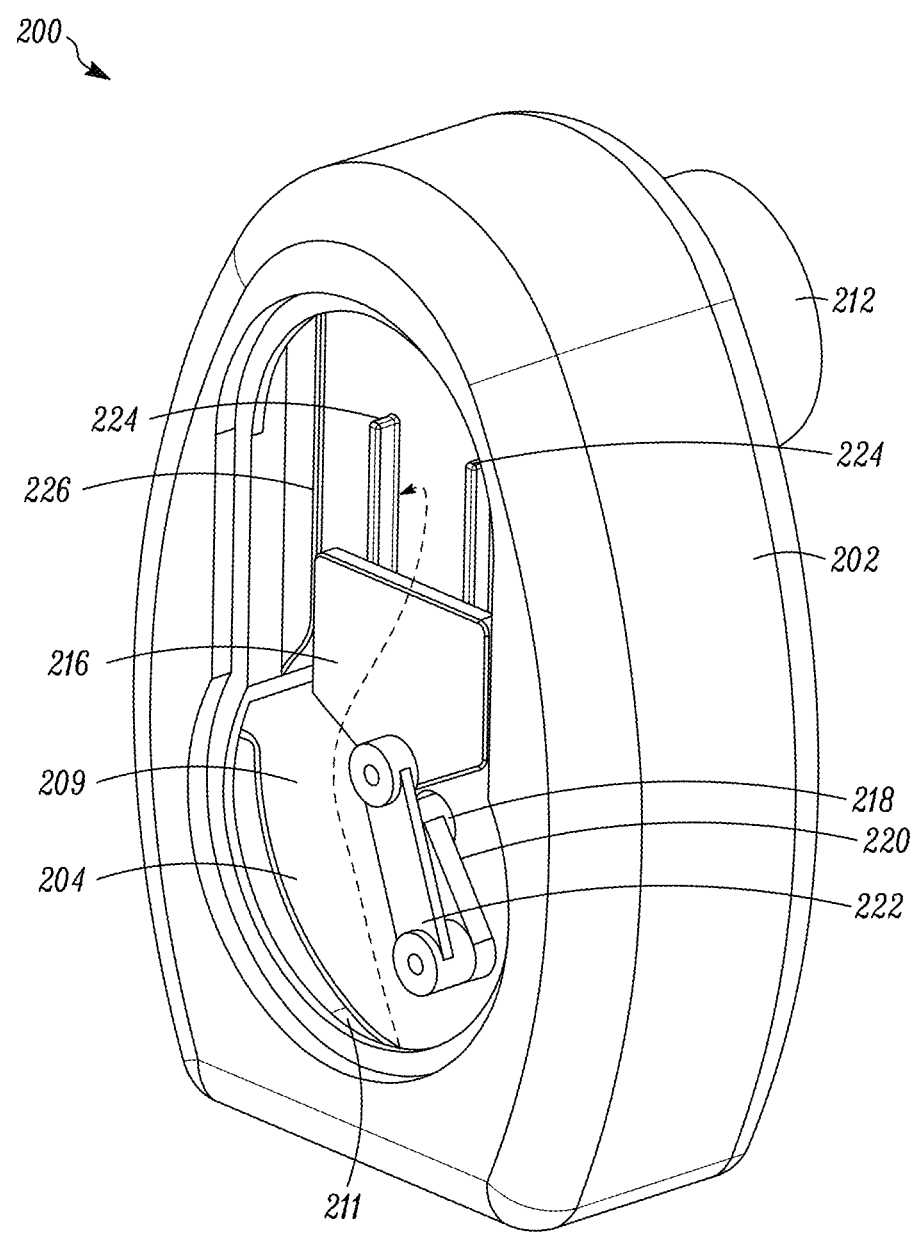
FIG. 12 is a perspective view of the OPEP device of the FIG. 7, shown with a rear cover of the device removed, and with a blocking member in an open position.
Figure 13:
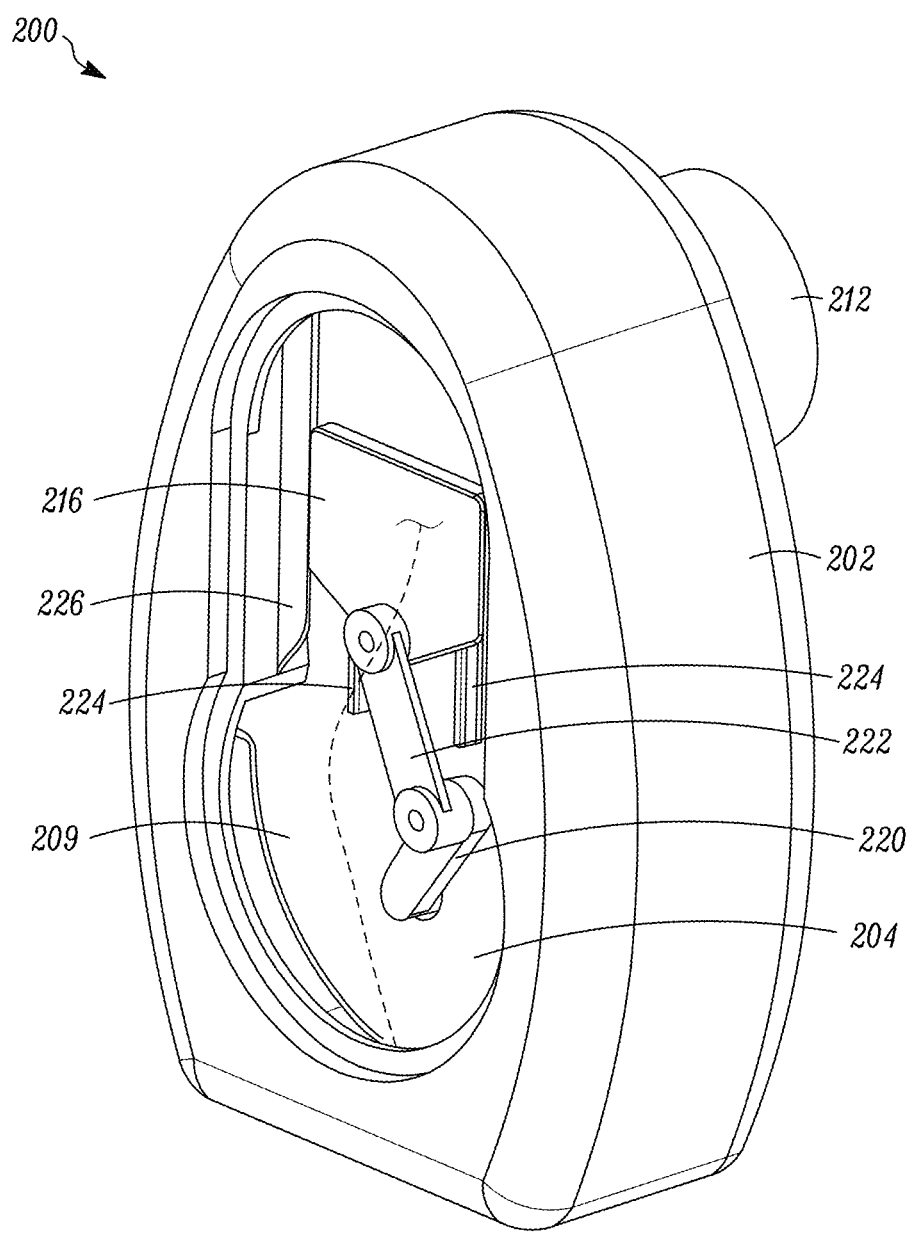
FIG. 13 is a perspective view of the OPEP device of FIG. 7, shown with the rear cover of the device removed, and with the blocking member in a closed position.
Figure 14:
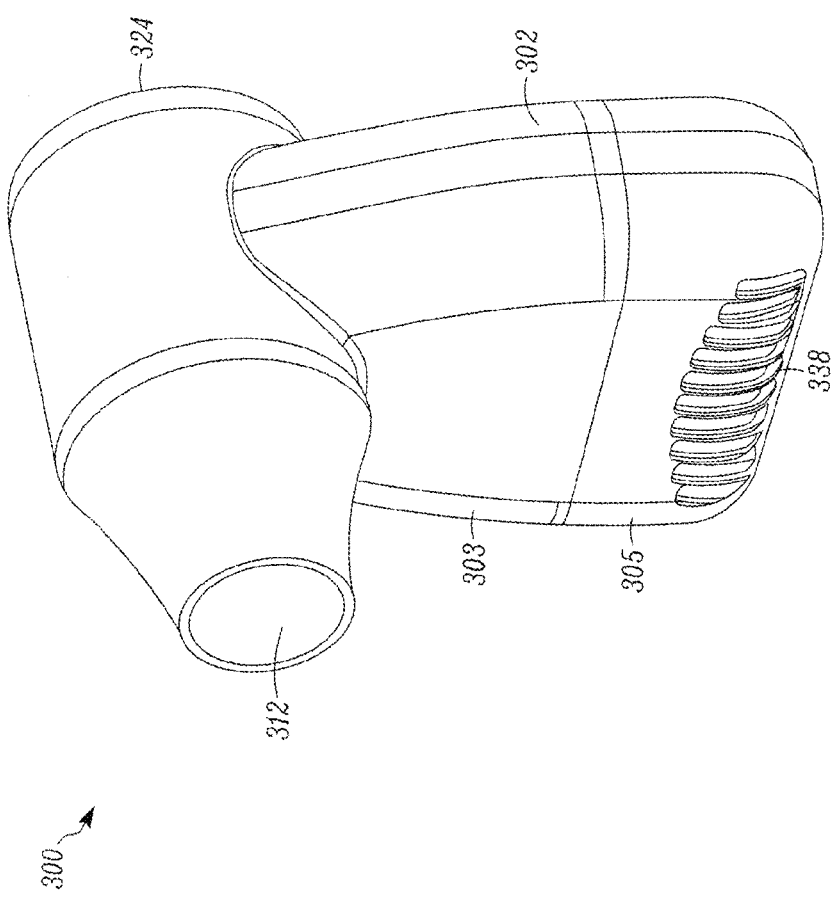
FIG. 14 is a front perspective view of a third embodiment of an OPEP device.

As shown in FIGS. 12-13, the first linkage 220, the second linkage 222, and the blocking member 216 are mounted within the second portion 209 of the chamber 204. The first linkage 220 is fixed about one end to the shaft 218, and as such, is configured to rotate in unison with the turbine 214. The second linkage 222 is hinged to the other end of the first linkage 220, as well as the blocking member 216. The blocking member 216 is surrounded by and in sliding engagement with a first pair and a second pair of guide rails 224, 226. In this way, rotation of the turbine 214 and shaft 218 causes rotation of the first linkage 220, translation and rotation of the second linkage 222, and ultimately, linear translation or reciprocation of the blocking member 216 between the position shown in FIG. 12 and the position shown in FIG. 13. In the position shown in FIG. 13, the blocking member 216 is in a closed position, where the flow of air through the chamber outlet 208 (seen in FIG. 8) is restricted by the blocking member 216, whereas, in the position shown in FIG. 12, the blocking member 216 is in a closed position, where the flow of air through the chamber outlet 208 is less restricted. It should be appreciated that the blocking member 216 may completely or partially restrict the flow of air through the chamber outlet 208 when the blocking member 216 is in a closed position.

The operation of the OPEP device 200 will now be described with reference to the illustrations shown in FIGS. 9-13. In FIGS. 9-13, the flow of air through the device 200 is illustrated by dashed lines. However, it should be appreciated that the dashed lines are exemplary and provided for purposes of illustration. The actual flow air through the device 200 may traverse any number of flow paths.

In general, administration of OPEP therapy using the OPEP device 200 begins with the blocking member 216 in an open position, as shown in FIG. 12. With the blocking member 216 in this position, as a user exhales into the mouthpiece 212, or user interface, exhaled air flows into the chamber 204 through the chamber inlet 206. In response to the flow of air through the chamber inlet 206, the turbine 214 begins to rotate, allowing the air to flow between the chamber inlet 206 and the passage 211 connecting the first portion 207 of the chamber with the second portion 209 of the chamber 204. Because the first linkage 220 is operatively connected to the turbine 214 via the shaft 218, rotation of the turbine 214 results in rotation of the first linkage 220, which in turn causing the second linkage 222 to rotate relative to the first linkage 220 and the blocking member 216, as the blocking member 216 is driven between an open position, shown in FIG. 12, and a closed position, shown in FIG. 13. As the blocking member 216 is moved from an open position shown in FIG. 12 to a closed position shown in FIG. 13, the air flowing from the passage 211 through the second portion 209 of the chamber 204 is restricted from exiting the chamber 204 through the chamber outlet 208, thereby causing the pressure throughout the device 200 to increase. As a user continues to exhale, and the turbine 214 continues to rotate, the blocking member 216 returns to an open position, allowing the air in the chamber 204 to exit the chamber 204 through the chamber outlet 208, resulting in a decrease in pressure throughout the device 200. During a period of exhalation, the blocking member 216 reciprocates repeatedly between an open position and a closed position, causing the pressure in the device to oscillate between a lower pressure and a higher pressure, which is in turn transmitted to the user's airways, thereby administering OPEP therapy.

Turning to FIGS. 14-19, a third embodiment of an OPEP device 300 is shown. In general, the OPEP device 300 includes a housing 302 enclosing a chamber 304, a chamber inlet 306, a chamber outlet 308, a vent 338, a mouthpiece 312 in communication with the chamber inlet 306, a turbine 314 rotatably mounted within the chamber 304 via a shaft 318, a blocking member 316, and a pair of arms 320, 322 operatively connected to the shaft 318.

The housing 302 and OPEP device 300 components may be constructed of any durable material, such as a low friction plastic or polymer, and may include an upper section 303, an inner section 301, and a lower section 305 that are removably attachable such that the chamber 304 may be periodically accessed for cleaning and/or replacement of the turbine 314. In addition, although the mouthpiece 312 is shown as being fixedly attached to the housing 302, it is envisioned that the mouthpiece 312 may be removeable and replaceable with a mouthpiece of a different shape or size. Preferably, the size or cross-sectional area of the mouthpiece 312 is greater than the size or cross-sectional area of the chamber inlet 306. It is envisioned that other user interfaces, such as breathing tubes or gas masks (not shown), may alternatively be associated with the housing 302.

Figure 16:
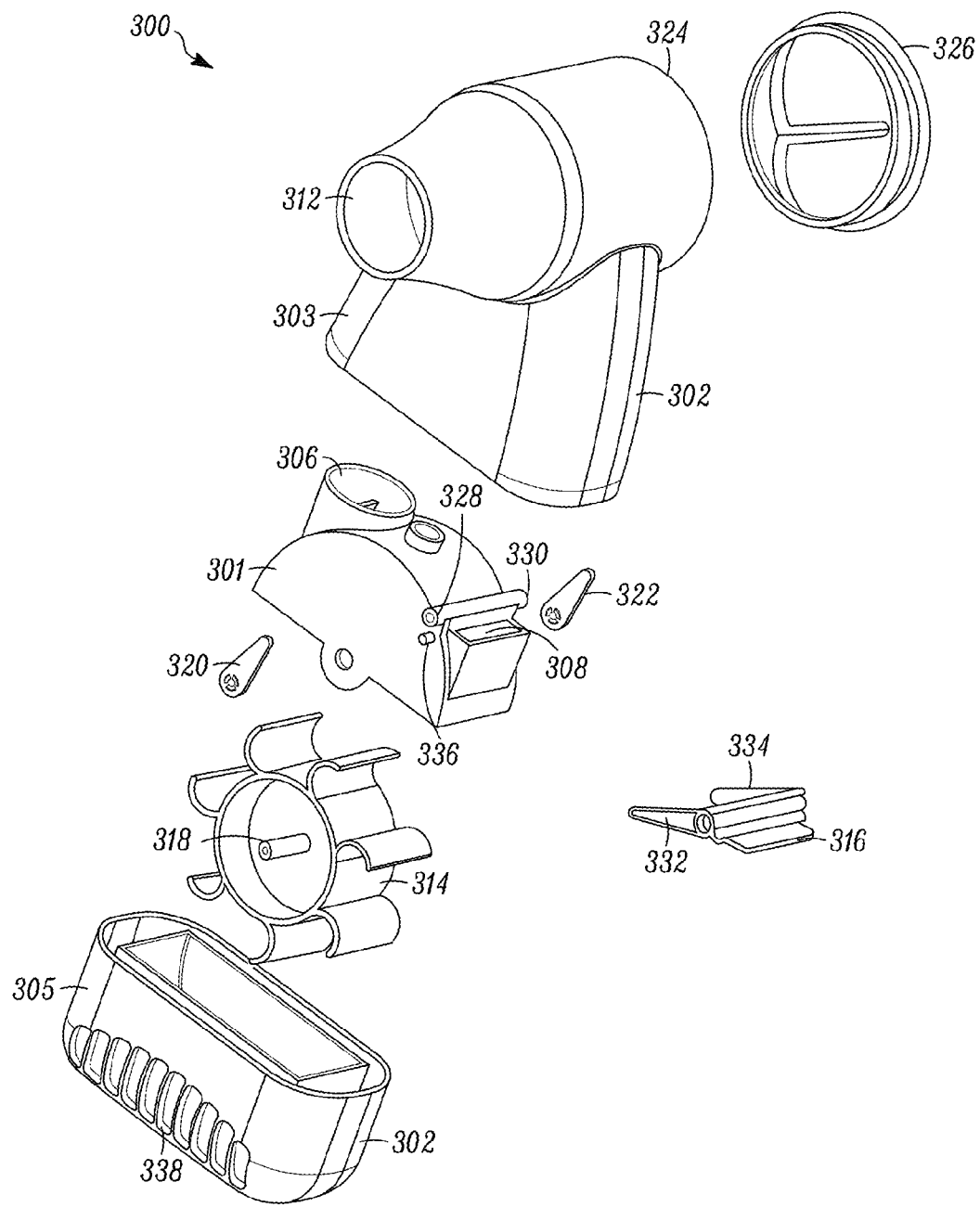
FIG. 16 is an exploded view of the OPEP device of FIG. 14.
Figure 17:
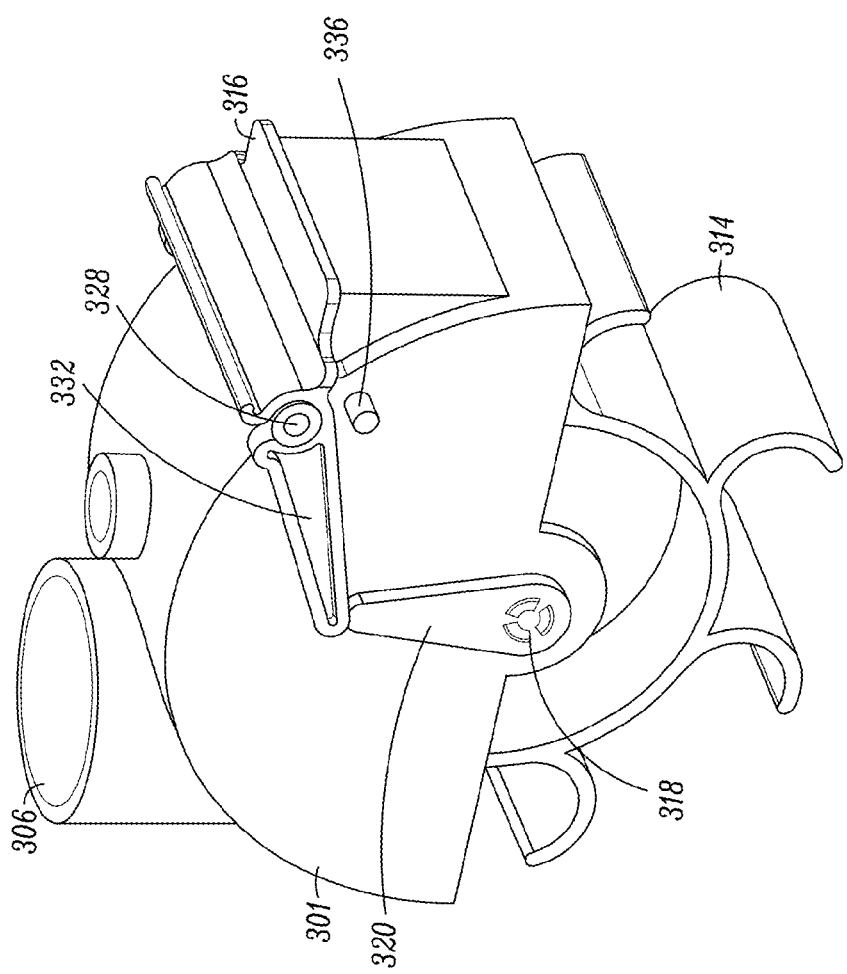
FIG. 17 is a perspective view of an assembly of the internal components of the OPEP device of FIG. 14.

Turning to FIG. 17, an assembly of internal components of the OPEP device 300 includes the turbine 314, the inner section 301 of the housing 302, the pair of arms 320, 322, and the blocking member 316. The turbine 314 is rotatably mounted via the shaft 318 within the inner section 301 of the housing 302, which partially forms the chamber 304, along with the lower section 305 of the housing 302. Like the turbine 214 in the OPEP device 200, the turbine 314 is configured to rotate in response to a flow of air through the chamber inlet 306, and could have as few as one vane, or many more vanes, the size and shape of which may vary. Each of the pair of arms 320, 322 (also shown in FIG. 16) are fixed to the shaft 318 such that rotation of the turbine 314 and the shaft 318 results in rotation of the arms 320, 322.

Figure 18:
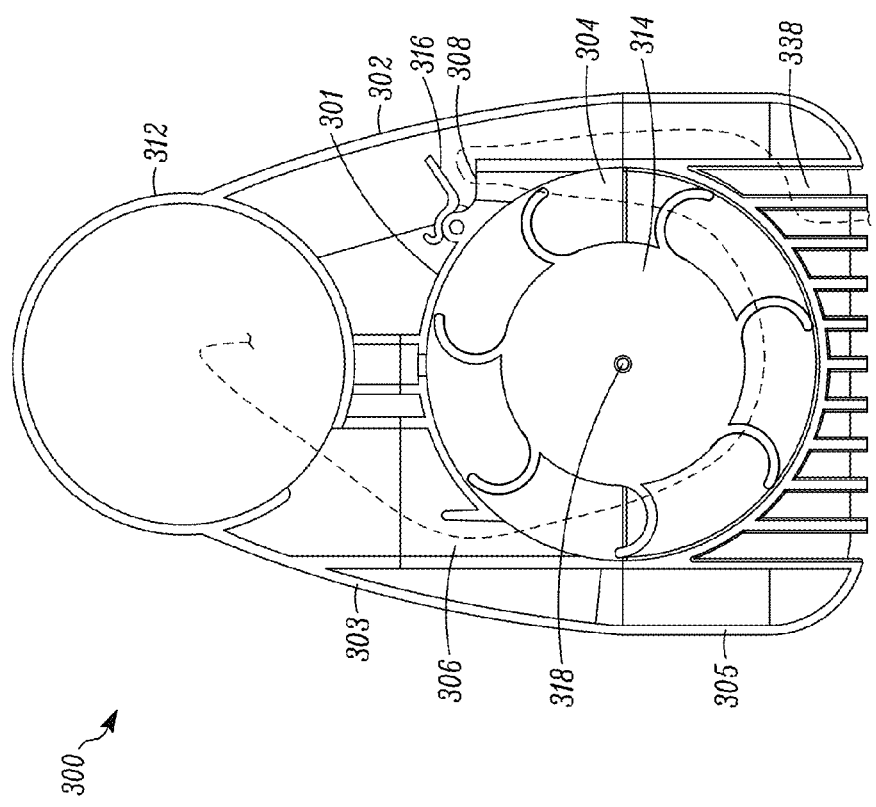
FIG. 18 is a cross-sectional view of the OPEP device of FIG. 14.

The blocking member 316 is mounted to the inner section 301 of the housing 302 about a pair of hinges 328, 330, such that the blocking member 316 may rotate relative to the chamber outlet 308 between a closed position, as shown in FIG. 17, where the flow of air through the chamber outlet 308 is restricted, and an open position, as shown in FIG. 18, where the flow of air through the chamber outlet 308 is less restricted. The blocking member 316 includes a pair of contact surfaces 332, 334 (also shown in FIG. 16) configured to periodically engage the pair of arms 320, 322 as the pair of arms 320, 322 rotate with the turbine 314 and the shaft 318, thereby moving the blocking member 316 from an open position to a closed position. The blocking member 316 also has a center of mass offset from the pair of hinges 328, 330, or the axis of rotation, such that when the contact surfaces 332, 334 are not engaged with the pair of arms 320, 322, the blocking member 316 moves to an open position, where the contact surfaces 332, 334 may engage a stop 336.

The operation of the OPEP device 300 will now be described with reference to the illustration shown in FIGS. 17-18. In FIG. 18, the flow of air through the device 300 is illustrated by a dashed line. However, it should be appreciated that the dashed line is exemplary and provided for purposes of illustration. The actual flow air through the device 300 may traverse any number of flow paths.

In general, administration of OPEP therapy using the OPEP device 300 begins with the blocking member 316 in an open position, as shown in FIG. 18. As a user exhales in to the mouthpiece 312, exhaled air travels through the housing 302 and enters the chamber 304 through the chamber inlet 306. In response to the flow of air through the chamber inlet 306, the turbine 314 begins to rotate, and exhaled air traverses the chamber 304, exiting the chamber 304 through the chamber outlet 308. Once exhaled air exits the chamber 304, it may travel through the housing 302 and exit the device 300 through the vent 338.

As a user continues to exhale, and the turbine 314 continues to rotate, the shaft 318 rotates, causing the pair of arms 320, 322 to also rotate. As the pair of arms 320, 322 rotate, they periodically engage the contact surfaces 332, 334 on the blocking member 316, as shown in FIG. 17, causing the blocking member 316 to rotate about the pair of hinges 328, 330 from an open position, shown in FIG. 18, to a closed position, shown in FIG. 17. As the blocking member 316 is moved from an open to a closed position, the air flowing through the chamber 304 is restricted from exiting the chamber 304 through the chamber outlet 308, thereby causing the pressure in the chamber 304 and the mouthpiece 312 to increase. As a user continues to exhale, and the turbine 314 continues to rotate, the pair of arms 320, 322 disengage the contact surfaces 332, 334, and the blocking member 316 returns to an open position, allowing the air in the chamber 304 to exit the chamber 304 through the chamber outlet 308, resulting in a decrease in pressure in the chamber 304 and the mouthpiece 312. During a period of exhalation, the blocking member 316 moves repeatedly between an open position and a closed position, causing the pressure in the device 300 to oscillate between a lower pressure and a higher pressure, which is in turn transmitted to the user's airways, thereby administering OPEP therapy.

Figure 15:
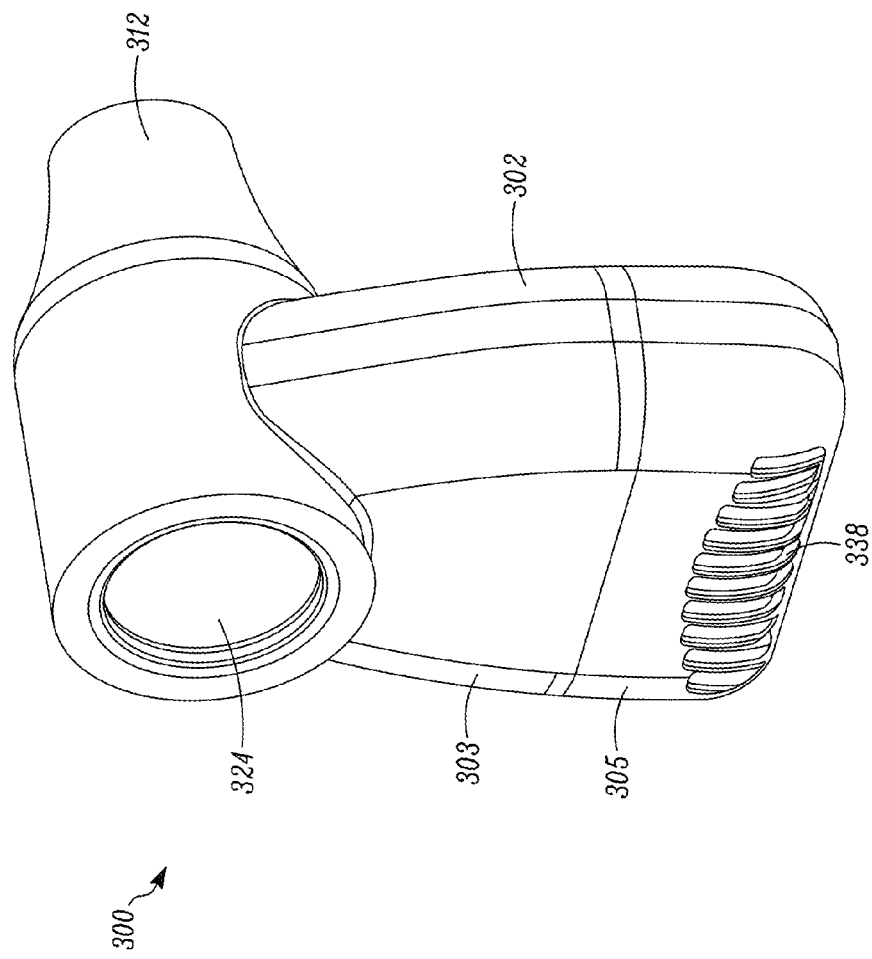
FIG. 15 is a rear perspective view of the OPEP device of FIG. 14.
Figure 19:
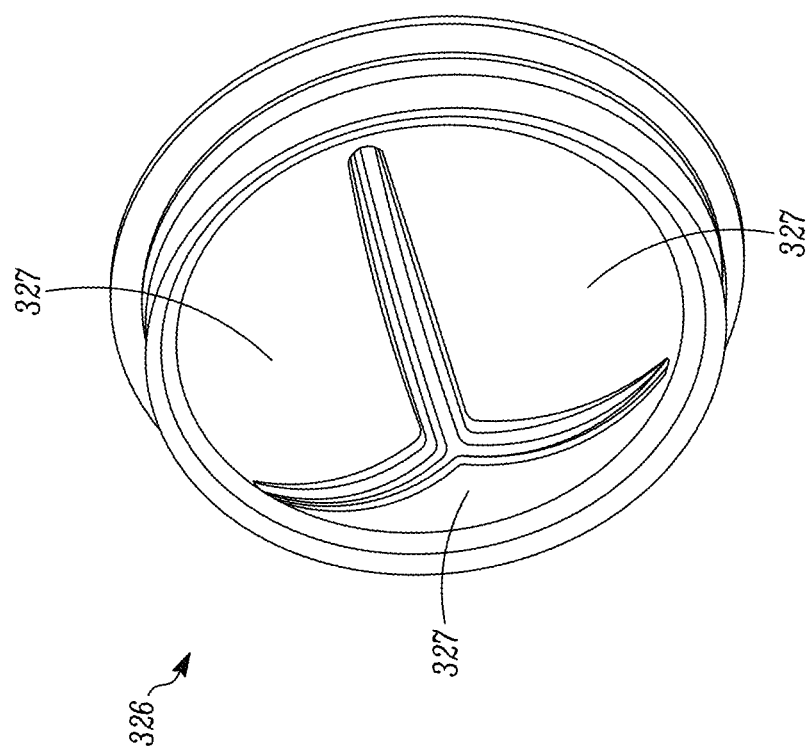
FIG. 19 is a perspective view of a one-way valve usable in the OPEP device of FIG. 14.

Finally, as best seen in FIG. 15-16, the OPEP device 300 is equipped with an inhalation portal 324 having a one-way valve 326, which is shown separately in FIG. 19. The one-way valve 326 includes a plurality of tabs or flaps 327 which are configured to open during a period of inhalation, thereby allowing air to travel through the inhalation portal 324 and the one-way valve 326, and close during a period of exhalation, thereby directing the flow of exhaled air through the chamber inlet 306. In this way, a user may exhale into the OPEP device 300 for the administration of OPEP therapy, as described above, and also inhale air surrounding the OPEP device 300 through the inhalation portal 324. Alternatively, the OPEP device 300 may be used in combination with a nebulizer for the combined administration of OPEP and aerosol therapies. Any of a number of commercially available nebulizers may be connected to the OPEP device 300 via the inhalation portal 324. One suitable nebulizer is the AeroEclipse® II breath actuated nebulizer available from Trudell Medical International of London, Canada. Descriptions of suitable nebulizers may also be found, for example, in U.S. Pat. No. 5,823,179, the entirety of which is hereby incorporated by reference herein. In this way, a user may exhale into the OPEP device 300 for the administration of OPEP therapy, as described above, and also inhale an aerosolized medicament from an attached nebulizer through the one-way valve 326 and the inhalation portal 324. While the inhalation portal 324 is shown in connection with the OPEP device 300, it should be appreciated that the OPEP device 100 and the OPEP device 200 could also include an inhalation portal and one way-valve configured to operate as described above.

Although the description of the embodiments described above refer to the administration of OPEP therapy on exhalation, it should be appreciated that such embodiments are also configurable for the administration of oscillating pressure therapy upon exhalation only, inhalation only, or both exhalation and inhalation. Accordingly, the terms "oscillating positive respiratory pressure" and "oscillating positive expiratory pressure," or "OPEP," may be used interchangeably. Similarly, the term "respiratory" may refer to inhalation, exhalation, or both inhalation and exhalation. Use of any such term should not be construed as a limitation to only inhalation or only exhalation.

The foregoing description of the inventions has been presented for purposes of illustration and description, and is not intended to be exhaustive or to limit the inventions to the precise forms disclosed. It will be apparent to those skilled in the art that the present inventions are susceptible of many variations and modifications coming within the scope of the following claims.

What is claimed is:

1. A respiratory treatment device comprising:
a housing enclosing a chamber;
a chamber inlet configured to receive a flow of air into the chamber through the chamber inlet;
a first chamber outlet configured to permit the flow of air to exit the chamber through the first chamber outlet;
a second chamber outlet configured to permit the flow of air to exit the chamber through the second chamber outlet;
a vane mounted within the chamber, the vane being configured to rotate in response to the flow of air through the chamber during a single period of exhalation repeatedly between a first position where the flow of air is directed to exit the chamber through the first chamber outlet, and a second position where the flow of air is directed to exit the chamber through the second chamber outlet;
a blocking member disposed on the vane, the blocking member moveable relative to the chamber inlet during the single period of exhalation repeatedly between a closed position where the flow of air through the chamber inlet is restricted, and an open position where the flow of air through the chamber inlet is less restricted.

2. The respiratory treatment device of claim 1, wherein the vane is prohibited from completing a complete revolution.

3. The respiratory treatment device of claim 1, wherein a size of the blocking member is greater than a size of the chamber inlet.

4. The respiratory treatment device of claim 1, wherein a size of the blocking member is less than a size of the chamber inlet.

5. The respiratory treatment device of claim 1, wherein an axis of rotation of the vane is offset from a center of the vane.

6. The respiratory treatment device of claim 1, furthering comprising a mouthpiece, wherein a cross sectional area of the mouthpiece is larger than a cross sectional area of the chamber inlet.

7. The respiratory treatment device of claim 6, further comprising an inhalation port in communication with the mouthpiece, the inhalation port comprising a one-way valve configured to open upon inhalation and close upon exhalation.

8. The respiratory treatment device of claim 1, wherein a cross-sectional area of the chamber inlet is less than at least one of a cross-sectional area of the first chamber outlet or a cross-sectional area of the second chamber outlet.

9. A respiratory treatment device comprising:
a housing enclosing a chamber;
an inlet configured to receive a flow of air into the chamber;
an outlet configured to permit the flow of air to exit the chamber;
a blocking member moveable relative to the outlet during a single period of exhalation repeatedly between a closed position where the flow of air through the outlet is restricted, and an open position where the flow of air through the outlet is less restricted;
at least one vane rotatably mounted in the housing, the at least one vane being configured to move the blocking member during the single period of exhalation repeatedly between the closed position and the open position in response to the flow of air; wherein the at least one vane comprises a turbine having a plurality of vanes; and wherein the blocking member is prohibited from completing a full revolution.

10. The respiratory treatment device of claim 9, wherein the blocking member is connected to the at least one vane by a shaft and at least one linkage.

11. The respiratory treatment device of claim 10, wherein the shaft and the at least one linkage cooperate to move the blocking member in linear reciprocating motion.

12. The respiratory treatment device of claim 9, wherein the blocking member is configured to reciprocate between the open position and the closed position in response to movement of an arm connected to the at least one vane.

13. The respiratory treatment device of claim 9, wherein the blocking member is biased toward the open position.

14. The respiratory treatment device of claim 9, wherein the chamber comprises a first portion enclosing the at least one vane and a second portion enclosing the blocking member.

15. The respiratory treatment device of claim 14, wherein the first portion is in communication with the second portion.

16. The respiratory treatment device of claim 9, further comprising a mouthpiece, wherein a cross sectional area of the mouthpiece is larger than a cross sectional area of the inlet.

17. The respiratory treatment device of claim 16, further comprising an inhalation port in communication with the mouthpiece, the inhalation port comprising a one-way valve configured to open upon inhalation and close upon exhalation.

18. The respiratory treatment device of claim 9, wherein a cross-sectional area of the chamber inlet is less than a cross-sectional area of the chamber outlet.

19. A method of performing respiratory treatment, the method comprising:
passing a flow of air through a device having an inlet configured to receive a flow of air into a chamber through the inlet, a first outlet configured to permit the flow air to exit the chamber through the first outlet, and a second outlet configured to permit the flow of air to exit the chamber through the second outlet;
rotating a vane mounted within the device in response to the flow of air through the device during a single period of exhalation repeatedly between a first position where the flow of air is directed to exit the chamber through the first outlet, and a second position where the flow of air is directed to exit the chamber through the second outlet; and,
moving a blocking member disposed on the vane relative to the chamber inlet during the single period of exhalation repeatedly between a closed position where the flow of air through the chamber inlet is restricted, and an open position where the flow of air through the chamber inlet is less restricted.

* * * * *